United States Patent [19]
Diamandis

[11] Patent Number: 5,679,534
[45] Date of Patent: Oct. 21, 1997

[54] DETECTION OF PROSTATE-SPECIFIC ANTIGEN IN AMNIOTIC FLUID, MATERNAL SERUM AND BREAST MILK

[76] Inventor: Eleftherios P. Diamandis, 44 Gerrard Street, West, Apt. 1504, Toronto, Ontario, M5G 2K2, Canada

[21] Appl. No.: 509,898

[22] Filed: Aug. 1, 1995

[30] Foreign Application Priority Data

Aug. 1, 1994 [GB] United Kingdom ............... 94 15489
Mar. 28, 1995 [GB] United Kingdom ............... 94 06317

[51] Int. Cl.$^6$ ............... G01N 33/573; G01N 33/577; C07K 16/40
[52] U.S. Cl. ............... 435/7.4; 436/510; 530/388.26; 530/388.85; 530/389.1
[58] Field of Search ............... 435/7.1, 7.4; 530/387.1, 530/388.1, 388.26, 388.85, 389.1, 389.7; 436/510

[56] References Cited

FOREIGN PATENT DOCUMENTS 2 187 283  9/1987  United Kingdom.
WO A 92
  01936   2/1992  WIPO.

OTHER PUBLICATIONS

Acta Cytologica, vol. 33, No. 6, 1989, F.C. Schmitt, pp. 899–902, "Cytology and Immunocytochemistry of Bilateral Breast Metastases from Prostratic Cancer".

Clinical Biochemistry, vol. 21, No. 3, Jun. 1988, pp. 139–150, Diamandis, E.P., "Immunoassays with Time-Resolved Fluorescence Spectroscopy: Principles and Applications".

Bas. App. Histochem., vol. 33, 1989, pp. 25–29, M. Papotti et al., "Immunocytochemical Detection of Prostate–Specific Antigen (PSA) in Skin Adnexal and Breast Tissues and Tumors".

Eur. J. Clin. Chem. Clin. Biochem. vol. 29, 1991, pp. 787–794, W.G. Wood et al., "The Establishment and Evaluation of Luminescent–Labelled Immunometric Assays for Prostate–Specific Antigen–alpha1–Antichymotrypsin Complexes in Serum".

Clinical Chemistry, vol. 39, No. 10, pp. 2108–2114, H. Yu et al., "Ultrasensitive Time–Resolved Immunofluorometric Assay of Prostate–Specific Antigen in Serum and Preliminary Clinical Studies".

*Primary Examiner*—Christina Y. Chan
*Assistant Examiner*—F. Pierre VanderVegt
*Attorney, Agent, or Firm*—Banner & Witcoff, Ltd.

[57] ABSTRACT

A method for the evaluation of the condition of a fetus by quantitative measurement of prostate specific antigen (PSA) is provided. In the method, a sample of amniotic fluid or maternal serum is obtained at a gestational week and the sample is assayed for the amount of PSA present. The amount of PSA in the sample is compared with the PSA mean for the given gestational week and evaluated for the risk of a phenotypic and/or genotypic disorder.

4 Claims, 10 Drawing Sheets

DETECTION OF PROSTATE-SPECIFIC ANTIGEN IN AMNIOTIC FLUID, MATERNAL SERUM AND BREAST MILK

FIELD OF THE INVENTION

This invention relates to the detection of prostate-specific antigen (PSA) in amniotic fluid and pregnant women's serum to provide information on the fetus well being and also the detection of PSA in breast milk to provide information on circulating maternal steroids.

BACKGROUND OF THE INVENTION

Prostate specific antigen (PSA), a 33 kDa serine protease, was until recently, only detected in normal, benign hypertrophic and malignant prostatic tissues, but not in other human tissues. It was discovered that PSA exists at elevated amounts in the sera of patients with prostate cancer and therefore considered to be a highly specific biochemical marker of prostatic epithelial cells (Lilja 1985, Armbruster 1993). U.S. Pat. No. RE. 33,405 describes this prostate antigen and the diagnosis of prostate cancer through detection of PSA. PSA was not found in the sera of normal healthy persons or patients with other forms of cancer. Furthermore, tissue extracts of non prostatic origin, whether normal or neoplastic, gave no immunologic reactivity with anti-prostate antigen antiserum. These tissues included liver, spleen, lung, bone marrow, bladder, breast, intestine, heart, pancreas, kidney, cerebral and cortex. PSA biochemistry and its clinical applications for prostate cancer screening, diagnosis and monitoring have recently been reviewed (Osterling 1991, Armbruster 1993).

Surprisingly PSA was later discovered in approximately 30% of breast tumors and it was established that PSA production by breast cells is mediated by steroid hormone receptors (Yu et. al., 1994). This discovery is described in PCT Patent application No. PCT/CA94/00267. The presence of prostate-specific antigen in breast tumors is associated with earlier disease stage, younger women, and better survival. Furthermore, we discovered that PSA production could be stimulated by steroids in non-PSA producing breast tumor cell lines (United Kingdom Patent Application No. 9401491.7, Yu et al., 1994).

SUMMARY OF THE INVENTION

We have discovered that PSA is present in amniotic fluid, breast milk and in the sera of pregnant women. The quantitative measurement of PSA in amniotic fluid or pregnant womens' sera provides an evaluation of the condition of a fetus. The quantitative measurement of PSA in breast milk provides an evaluation of steroids circulating in the blood post-delivery and the rate of their metabolism.

An object of the invention is to provide a process for evaluating the condition of a fetus by quantitatively measuring the level of PSA in amniotic fluid or pregnant women's sera.

An object of invention is to provide a process for evaluating levels of circulating steroids in a woman's blood and the rate of their metabolism post-delivery.

According to an aspect of the invention, a method of quantitatively measuring PSA in amniotic fluid comprises:
a) providing a sample of amniotic fluid from a pregnant woman, and
b) assaying for the amount of PSA.

According to another aspect of the invention, a method of quantitatively measuring PSA in a pregnant woman's serum comprises:
a) providing a sample of serum from a pregnant woman, and
b) assaying for the amount of PSA.

According to another aspect of the invention, in a prenatal evaluation of fetal phenotypic and/or genotypic disorders, the steps of:
 i) providing a sample of amniotic fluid or maternal serum from a pregnant woman;
 ii) conducting a biological assay of the sample to detect the presence of PSA;
 iii) upon quantifying the level of PSA in the sample, comparing the PSA level with the PSA mean for the gestational week; and
 iv) classifying the pregnant woman as a high or low-risk for carrying a fetus with a phenotypic and/or genotypic disorder.

According to another aspect of the invention is a prenatal assay for determination of fetal gestational age, the assay comprising the steps of:
 i) providing a sample of amniotic fluid or maternal serum from a pregnant woman;
 ii) conducting a biological assay of the sample to detect the presence of PSA;
 iii) upon quantifying the level of PSA in the sample comparing with a standard mean of PSA concentration determined at each gestational week; and
 iv) classifying the fetus as a particular gestational age.

According to another aspect of the invention, a method of quantitatively measuring PSA in breast milk comprises:
a) providing a sample of breast milk, and
b) assaying for the amount of PSA.

According to an aspect of the invention, a method is provided for measuring PSA based on time resolved fluorometry (TR-FIA) (Diamandis 1988, He and Diamandis 1993) which is approximately 10–20 fold more sensitive than the commercially available and widely used immunometric techniques.

This method has been thoroughly evaluated and has an analytical detection limit of 0.002 µg/L and a biological detection limit of 0.01 µg/L of PSA in a test sample solution.

In accordance with the preferred aspect of the invention, an ultra-sensitive detection method for prostate-specific antigen in an amniotic fluid sample, pregnant woman's serum sample, or breast milk sample involving time resolved fluoroimmunoassay is provided. An amniotic fluid sample, pregnant woman's serum sample or breast milk sample is incubated with monoclonal anti PSA antibody. Biotinylated, polyclonal antibody specific to PSA is added to bind to any bound PSA. Alkaline phosphatase-labelled streptavidin (SA-ALP) is added. The activity of ALP is measured by adding the substrate 5-fluorosalicyl-phosphate and then adding $Tb^{3+}$-EDTA to form a fluorescent chelate. Fluorescence is measured during a specific time interval to indicate the amount of PSA. The amount of PSA detected allows one to evaluate the condition of a fetus.

BRIEF DESCRIPTION OF DRAWINGS

FIG. 4D is a Y-scale expansion of FIG. 4C.

DETAILED DESCRIPTION OF THE PREFERRED EMBODIMENTS

Figure 1:
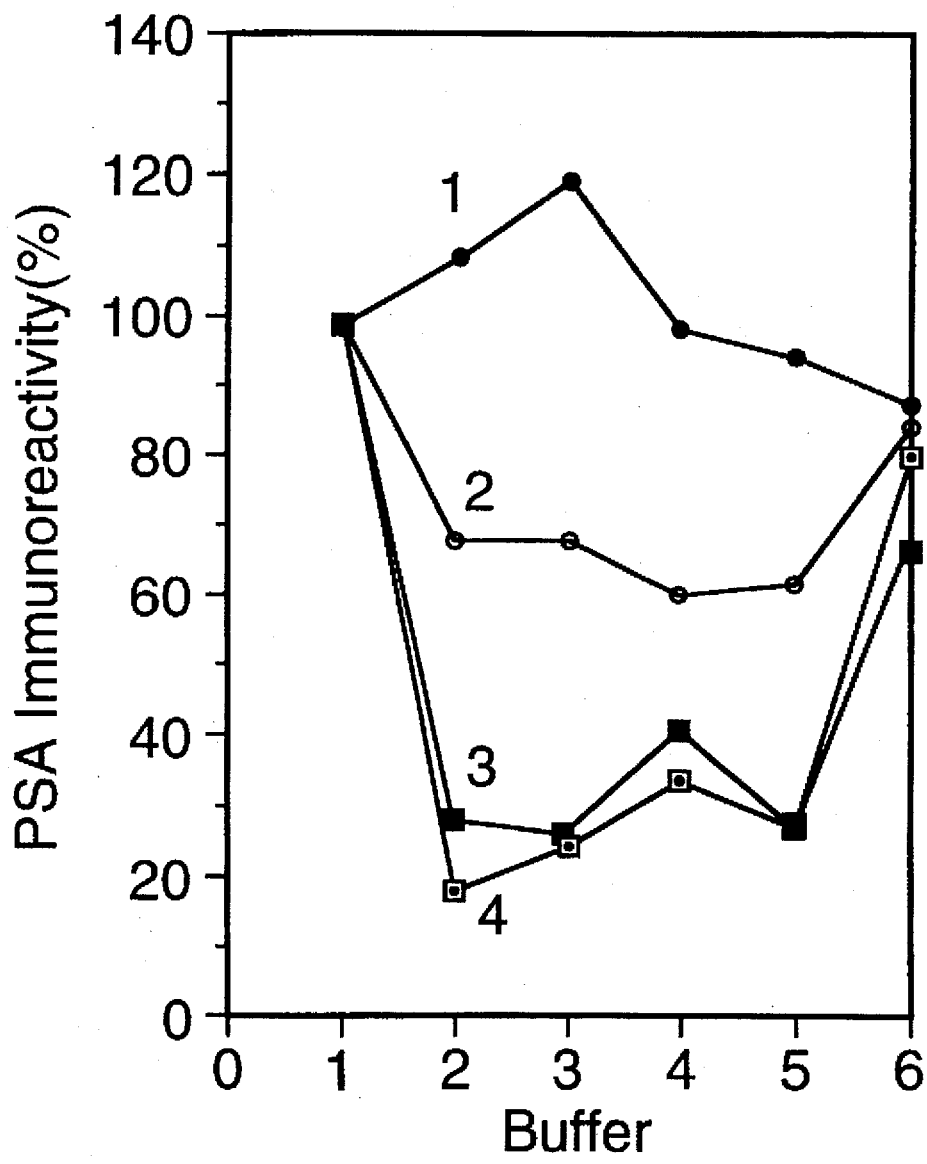
FIG. 1: Effect of assay buffer composition on amniotic fluid IR-PSA values.

Until very recently, PSA was considered one of the most specific biochemical markers for the prostate and was thought to be produced exclusively by the epithelial cells of the prostate (Osterling 1991, Armbruster 1993). There is now convincing evidence that PSA may have important, previously unrecognized biological functions including growth factor regulation (Cohen et. al., 1992, Kanety et. al., 1993, Killian et. al., 1993). Our discovery of PSA in breast tumors (Diamandis et. al., 1994, Diamandis and Sutherland 1994) which was found to be mediated through the action of the steroid hormone receptors (Yu et. al., 1994) was very surprising. We have further discovered that the PSA gene could be expressed in situations of steroid hormone overproduction, namely pregnancy. It is known that the placenta produces massive amounts of steroids during pregnancy (Ashwood 1994). Surprisingly, PSA was found in amniotic fluid and its concentration increased with gestational age. The discovery of PSA in amniotic fluid, especially at relatively high concentrations at 14–22 gestational weeks, indicates a biological role for this protein in fetal growth and development. In addition, pregnant women were found to have elevated serum PSA in comparison to non-pregnant women and PSA was found in breast milk, declining to very low levels six days after delivery.

The presence of PSA in steroid hormone dependent prostate and breast tumors suggests that PSA plays a role as a growth factor regulator in cancer. The presence of PSA in amniotic fluid suggests a role for PSA as a growth factor regulator in normal fetal development.

PSA immunoreactivity was detected in all amniotic fluid samples tested. The PSA levels were very low at gestational ages of 11 to 13 weeks and increased as pregnancy progressed to 22 weeks. At term the amniotic fluid PSA concentration returned to very low levels. PSA in amniotic fluid is predominantly in its free 33 KDa form with a minor fraction (<20%) being present as PSA bound to $\alpha_1$-antichymotrypsin and possibly negligible amounts in complexes between PSA and $\alpha_2$-macroglobulin. No significant relationship exists between the level of PSA and amniotic fluid alpha-fetoprotein (AFP) or maternal serum AFP in samples with high AFP.

An analysis of PSA in fetal cord of blood serum at term demonstrated that the levels of PSA are very low in most samples. Serum samples from pregnant women with fetuses at gestational ages 15 to 20 weeks have significantly higher PSA levels than non-pregnant women under the age of 50. In comparison, in an extensive study of PSA presence in 674 sera from normal women, the overall prevalence of PSA levels $\geq 0.050$ µg/L was 1.6% (Yu and Diamandis 1994). The positivity rate dropped to 0.9% for normal women under the age of 50. However, in accordance with this invention PSA levels $\geq 0.50$ µg/L were found in 35% of pregnant women sera.

A further 571 sera were analyzed of which 312 were from non-pregnant women, and PSA concentration was plotted against completed gestational age. Samples depicted at gestational age 0 represent the PSA concentrations of sera from non-pregnant women. From the 312 sera from non-pregnant women, 167 (54%) had PSA concentrations $\leq 0.001$ µg/L. Only 36 sera from pregnant women (14%) had PSA concentration $\leq 0.001$ µg/L. At the level of 0.002 µg/L the percentages of PSA-negative sera from non-pregnant and pregnant women were 60% and 18%, respectively. At the cutoff level of 0.01 µg/L which is the biological detection limit of the assay, the percentages of PSA-negative sera from the non-pregnant and pregnant women were 82% and 48% respectively. Serum PSA concentrations in pregnant women are significantly higher than the serum PSA concentrations of non-pregnant women. Maternal serum PSA concentration seems to increase with gestational age up to gestational week 19 and declines thereafter.

The source of PSA in the serum of pregnant women is unknown but it could either come through diffusion of PSA from amniotic fluid or through production by the periurethral glands (Kamoshida and Tsutsumi 1990, Frazier et. al., 1992, Iwakiri et. al., 1993) or the breasts after stimulation by steroids produced by the placenta.

It was found that PSA could be proteolytically destroyed at least in some amniotic fluids. This could be a means for controlling the activity of PSA which is postulated to be a growth factor regulator.

Figure 9:
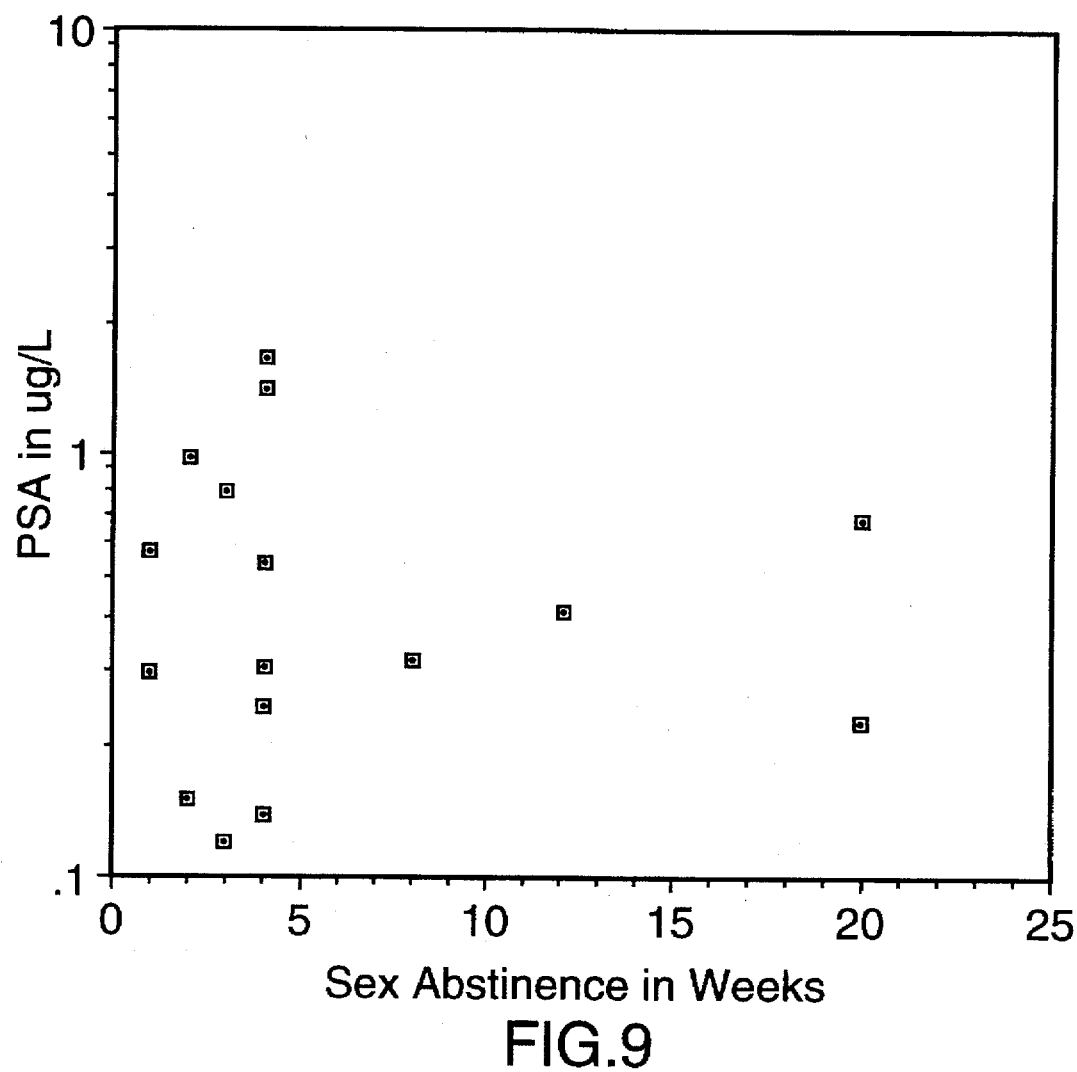
FIG. 9: Amniotic fluid PSA concentration in 16 amniotic fluids collected at term versus the time of abstinence from sexual intercourse in weeks.

Since it was surprising to find PSA in amniotic fluid, it was important to determine if it came from another source. There is a possibility that PSA enters the amniotic fluid by diffusion of sperm, which is very rich in PSA, through sexual contact during pregnancy. Amniotic fluids were collected during labour and used to examine the association between PSA concentration and length of maternal abstinence from sexual intercourse. The results of PSA analysis along with data on maternal abstinence from sexual activity are shown in FIG. 9. It appears that there is no relation between PSA levels and length of abstinence from sex before labour. At term, two patients with only one week of sexual abstinence before delivery had relatively low PSA levels and one patient with 20 weeks abstinence had levels which were 6–10 fold higher.

We found that the gender of the fetus was also not associated with the PSA concentration in amniotic fluid. From the 157 fetuses with known gender, 73 were females and 84 were males. The median PSA concentration in females was 0.37 µg/L and in males was 0.24 µg/L.

The possible association between amniotic fluid PSA concentration and maternal age was also investigated. The maternal age effect was examined by categorizing patients with known age in three age groups; i.e. <35 years (total of 178 patients), 35–36 years (183 patients) or >36 years (200 patients). Amniotic fluid PSA concentration was categorized in four groups; i.e. PSA <0.098 µg/L (142 patients), 0.098–0.22 µg/L (134 patients), 0.23–0.55 µg/L (131 patients) and 0.55 µg/L (154 patients). Analysis at three different gestational age groups (i.e. <15 weeks, 15–16 weeks, >16 weeks) revealed no statistically significant association between PSA concentration and maternal age.

Some amniotic fluid samples were initially analyzed for PSA using our ultrasensitive assay (Yu and Diamandis 1993) and various combinations of assay buffers. This study has shown that in order for the immunoreactive PSA (IR-PSA) in amniotic fluid to be quantitatively analyzed, the assay buffer should preferably be identical in composition to that reported for serum samples, that is, containing 0.5 mol KCl and 5 ml Tween 20 per liter, in addition to 60 g/L of bovine serum albumin (BSA). If Tween 20 is not included in the assay buffer, the IR-PSA is underestimated, suggesting that PSA in amniotic fluid may be loosely bound to amniotic fluid components. This binding can also be eliminated by dilution of the amniotic fluid. The experimental data is shown in FIG. 1. FIG. 1 demonstrates the effect of assay buffer composition on amniotic fluid IR-PSA values. Assay buffers all contain the same quantity of named ingredient as Buffer 1 unless specified otherwise. Buffer 1 contains 60 g of bovine serum albumin (BSA), 0.5 mol of KCl, 5 g of Tween 20 and 50 mL of normal mouse serum per liter. Buffer 2 contains only BSA; Buffer 3 contains BSA and KCl; Buffer 4 contains BSA and mouse serum; Buffer 5 contains only 10 g/L of BSA and Buffer 6 contains BSA and Tween 20. The IR-PSA values obtained with Buffer 1 were considered as 100%. Samples 2, 3 and 4 were analyzed undiluted and contained 2.17, 0.21 and 0.26 µg/L of IR-PSA, respectively. Sample 1 contained 500 µg/L of IR-PSA and was analyzed after 100-fold dilution in the respective buffer. Recovery studies, performed by spiking amniotic fluids with purified seminal plasma PSA, have shown that recovery was incomplete (20–60%) if assay buffer containing only BSA was used. Recovery was almost complete when seminal plasma PSA or PSA from the serum of a prostate cancer patient were added to amniotic fluids and analyzed with assay buffer 1, as shown in FIG. 1. Results of recovery studies under these conditions are shown in Table 1. Mean recovery was 89+/–14% when spiking with seminal PSA and 101+/–6% when spiking with a prostate cancer patient serum. Dilution linearity was checked by analyzing one serum sample and five amniotic fluids either undiluted or diluted up to 32-fold. The data are shown in Table 2, confirming good linearity in all cases.

A group of 115 amniotic fluid samples were analyzed for immunoreactive PSA with our ultrasensitive assay (Espana et. al., 1991). For most of these samples information was also available on amniotic fluid AFP values, gestational age and maternal age. All amniotic fluid samples had detectable IR-PSA ranging from 0.012 µg/L to 16 µg/l, with the exception of one sample with IR-PSA concentration of 500 µg/L. The 5th, 10th, 25th, 50th, 75th, and 90th percentiles for IR-PSA levels in these amniotic fluids were 0.039, 0.055, 0.13, 0.34, 0.93 and 2.11 µg/L. There was a weak negative correlation between IR-PSA and amniotic fluid AFP. There was a positive correlation between IR-PSA and gestational age and the known negative correlation between amniotic fluid AFP and gestational age after 15 weeks gestation was confirmed. A correlation between amniotic fluid AFP and maternal age was also observed. These correlation studies are summarized in Table 3.

Figure 2A:
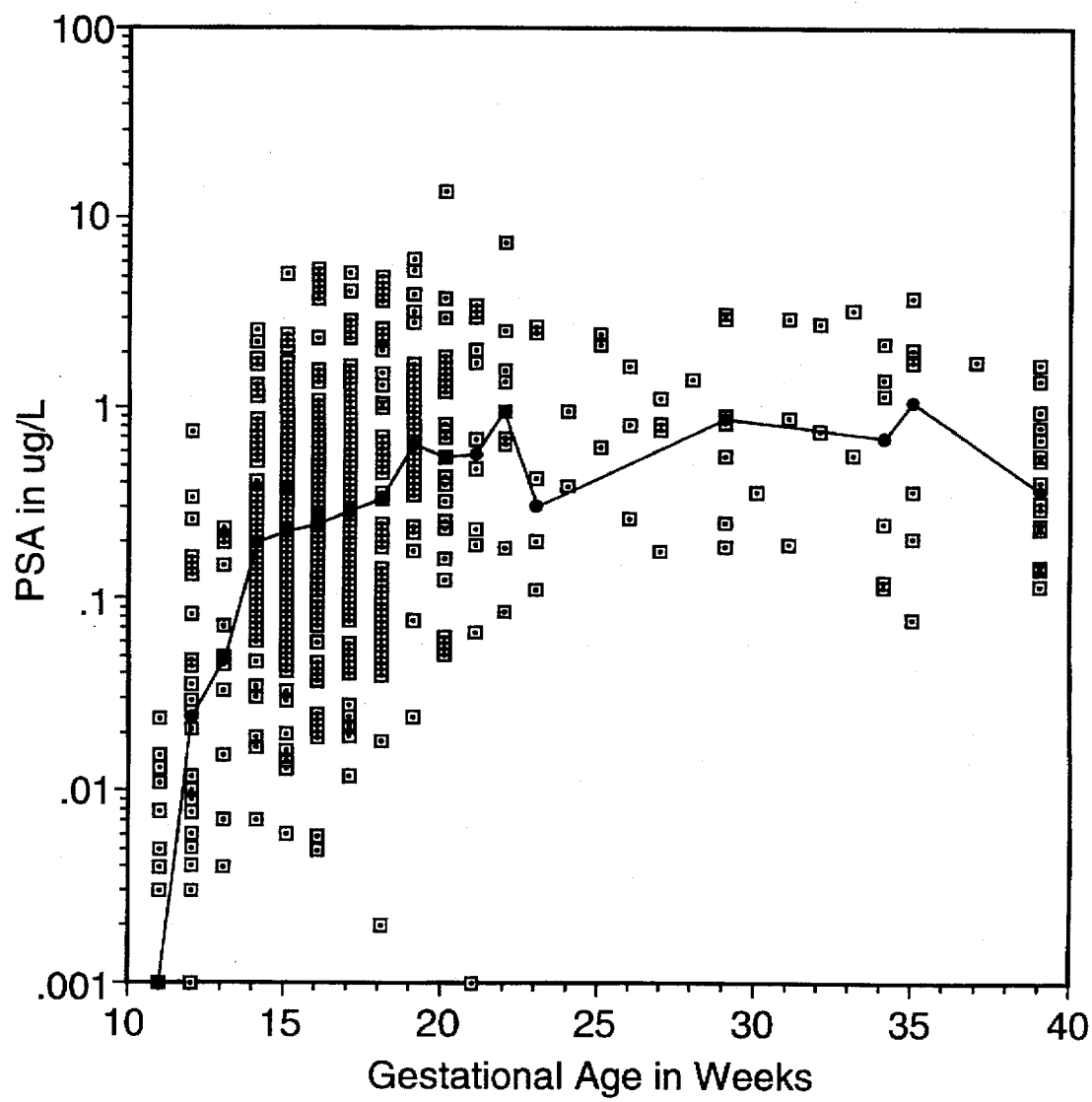
FIG. 2a: PSA concentration in amniotic fluids versus the completed gestational week.
Figure 2B:
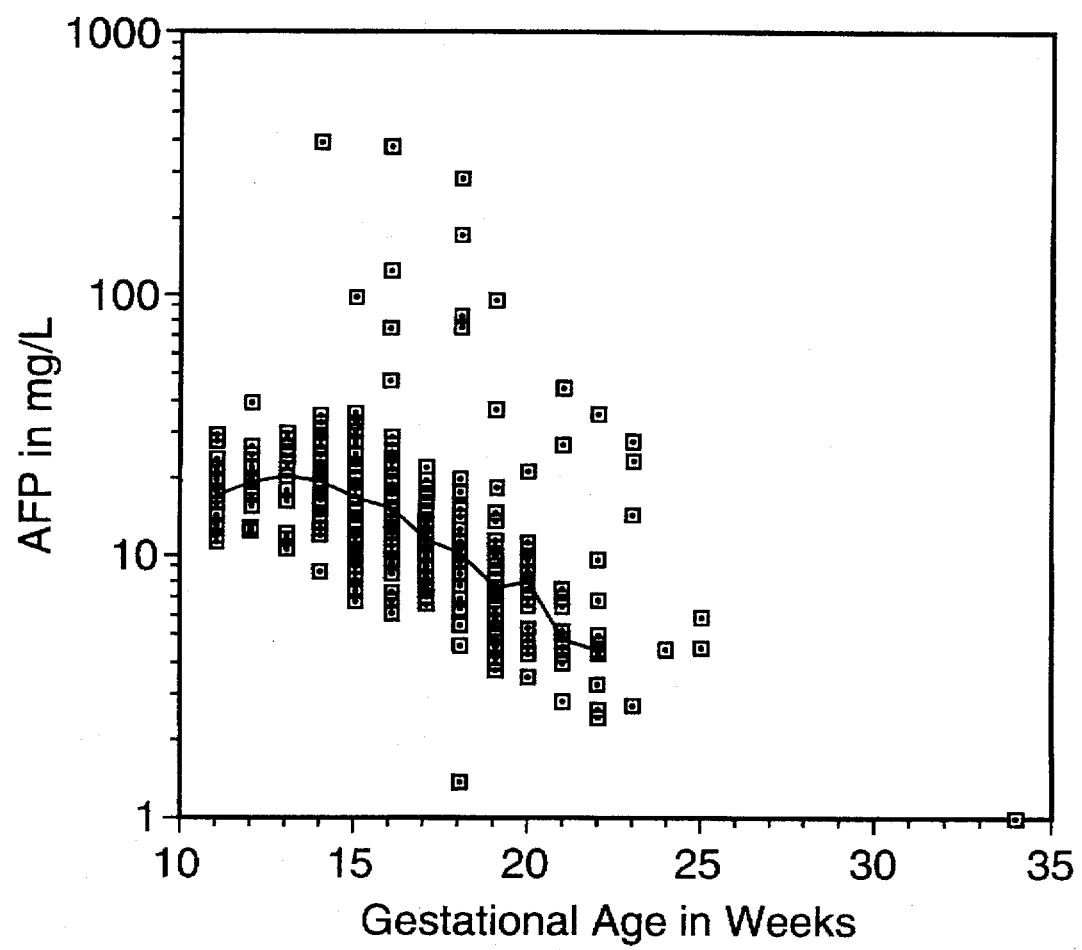
FIG. 2b: AFP concentration in amniotic fluids versus the completed gestational week.

Both PSA (N=829) and AFP (N=770) values in amniotic fluid were plotted versus the gestational age and the results are shown in FIGS. 2(a) & (b). The median values are connected with a solid line in both cases. Values were assigned on the basis of completed gestational weeks. Amniotic fluid AFP levels decline after the 15th gestational week as previously reported (Diamandis 1988). However as per this invention, it has now been found that PSA levels tend to increase with gestational age. PSA levels were very low before the gestational age of 12–13 weeks. Numerical data on the median values per gestational week are presented in Table 6.

Thirty three cord blood sera collected during delivery were also analyzed. Of these, 31 had serum IR-PSA levels <0.05 µg/L; only two sera had values of 0.098 and 0.17 µg/L. Maternal sera at gestational ages between 15–20 weeks were also analyzed for IR-PSA. From the 43 samples tested, 15 (35%) had IR-PSA levels ≧0.050 µg/L and 6 (14%) had PSA levels ≧0.10 µg/L with a maximum value of 0.34 ug/L. In a previous study, involving 674 normal females, we found IR-PSA ≧0.050 µg/L in only 2% of women of all ages by using the same method and IR-PSA ≧0.10 µg/L in 1% of women (Yu and Diamandis 1994). Values ≧0.10 µg/L were seen in only one out of 572 women under the age of fifty (Yu and Diamandis 1994).

No apparent relationship was found between amniotic fluid IR-PSA levels and AFP levels in patients with highly elevated AFP either in amniotic fluid or in maternal serum. For this study, we tested four amniotic fluids with AFP levels 3–21 times the median for the gestational age and four maternal sera with AFP levels 4–10 times the median for the gestational age (Table 4).

Figure 3:
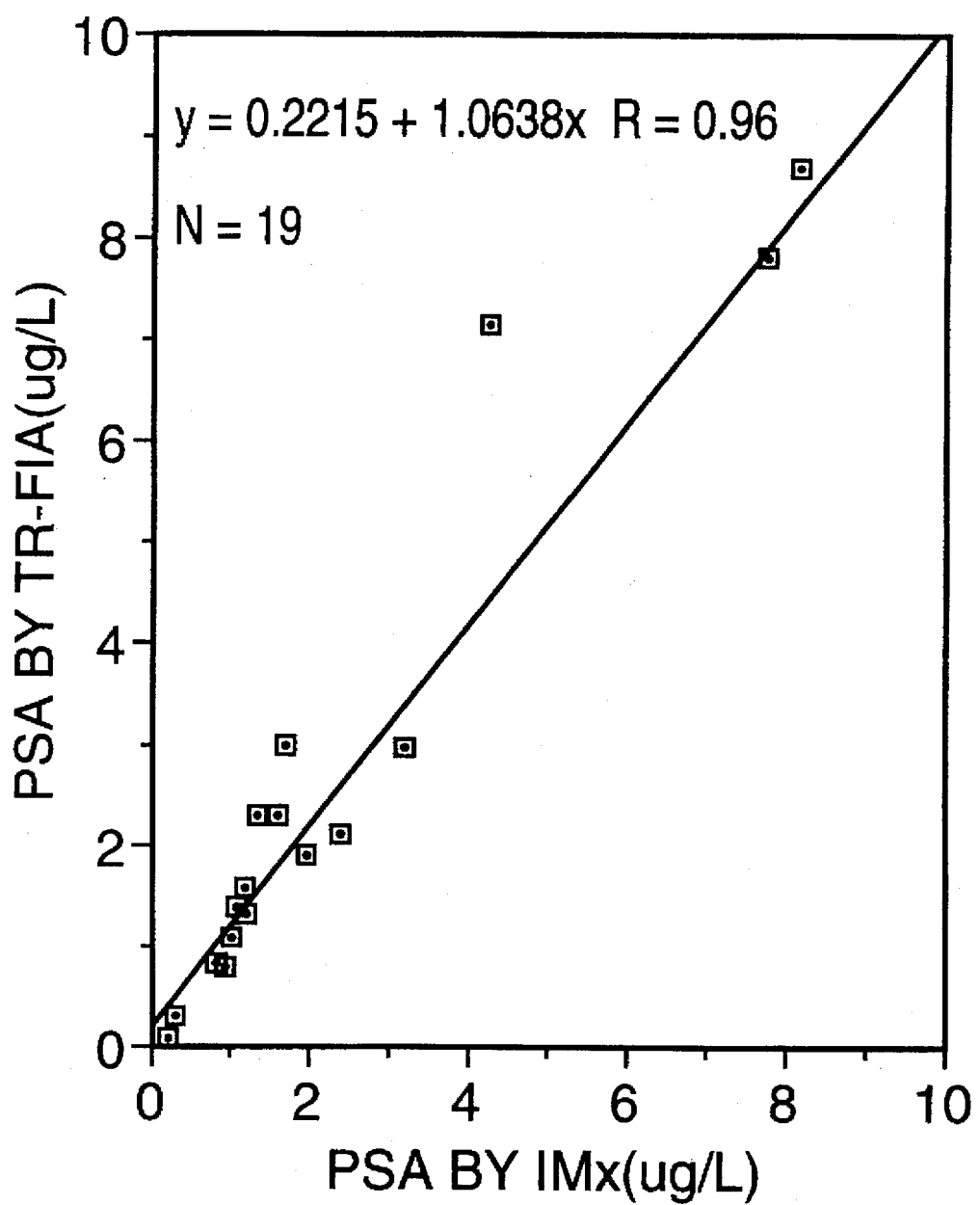
FIG. 3: Correlation of PSA results between our TR-FIA immuno-fluorometric assay (Yu and Diamandis 1993) and the commercially available IMx PSA assay (Vessela et. al., 1992) for 19 amniotic fluids. R=Pearson correlation coefficient.

Nineteen amniotic fluids were analyzed by our method and by the IMx PSA assay, an automated and widely used assay commercially available by Abbott Laboratories (Vessela et. al., 1992). The results are shown in FIG. 3. One amniotic fluid sample with the highest IR-PSA immunoreactivity was also analyzed in dilution and found to contain 500 µg/L by our method and 440 µg/L by the IMx method. The two methods correlate and agree very well.

High performance liquid chromatography (HPLC) of amniotic fluids has revealed that IR-PSA is present in at least two forms (FIG. 4). FIG. 4A is the HPLC separation of an amniotic fluid with a PSA concentration of 500 µg/L. PSA immunoreactivity was determined in fractions with the immunofluorometric procedure (●) (Yu and Diamandis 1993) or with an assay that measures the PSA $\alpha_1$-antichymotrypsin complex (ACT-PSA) (♦). Free PSA elutes at fraction 38 (approximately 33 KDa) and the PSA-$\alpha_1$-antichymotrypsin complex (ACT-PSA) at fraction 30 (approximately 100 KDa). FIG. 4B is the HPLC of a serum sample from a prostate cancer patient with a PSA concentration of 100 µg/L. There is a prominent ACT-PSA peak and a minor peak corresponding to free PSA. Other symbols as in FIG. 4A. FIG. 4C is the HPLC of another amniotic fluid (which was previously preconcentrated to 80 µg/L with ultrafiltration as described elsewhere (Yu et. al., 1994). Expansion of the y scale in FIG. 4D reveals a small PSA-containing peak of unknown identity at fraction 25 in addition to peaks at fractions 30 and 38. The column was calibrated with a molecular weight standard from BioRad Labs eluting at fraction 20 (660 KDa), 28 (160 KDa), 35 (44 KDa), 40 (17 KDa) and 47 (1.4 KDa). Flow-rate was 0.5 mL/min.

Figure 4A:
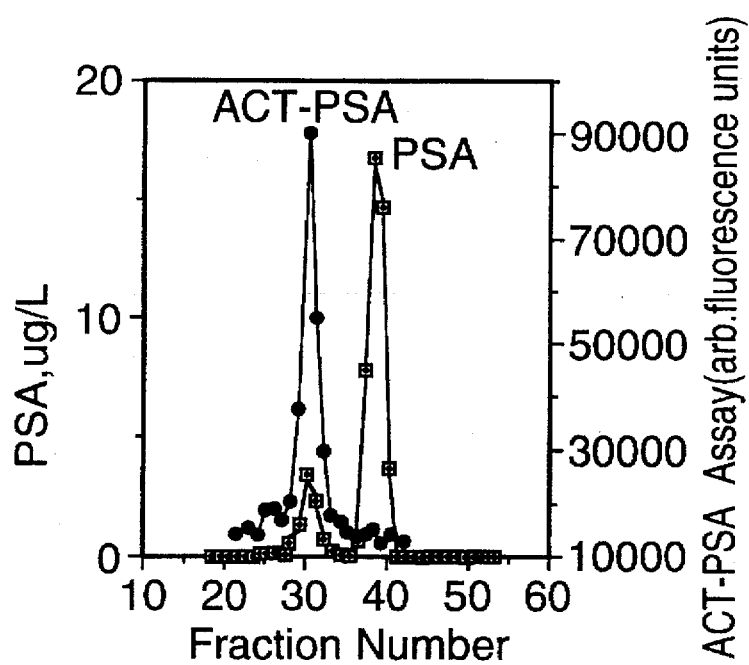
FIGS. 4A–4D: High performance liquid chromatographic separation of PSA-containing amniotic fluids (FIGS. 4A and 4C) and serum (FIG. 4B).
Figure 4B:
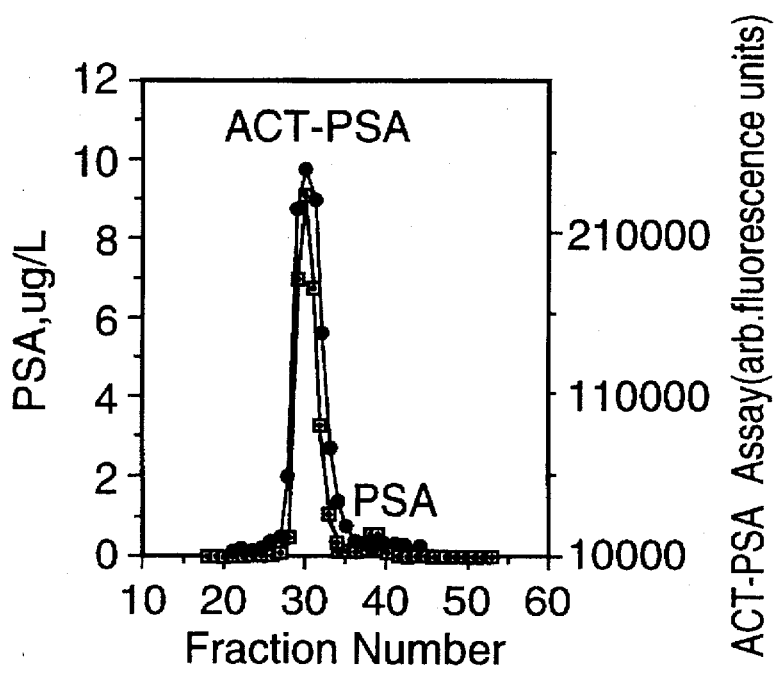
Figure 4C:
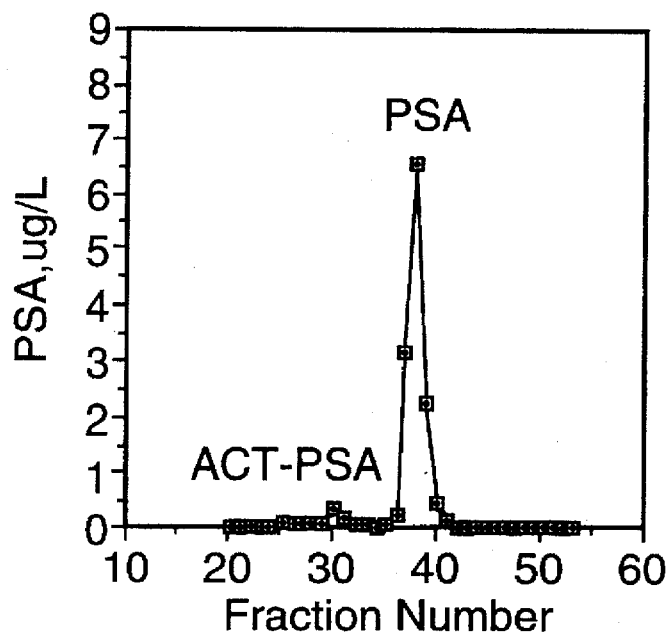
Figure 4D:
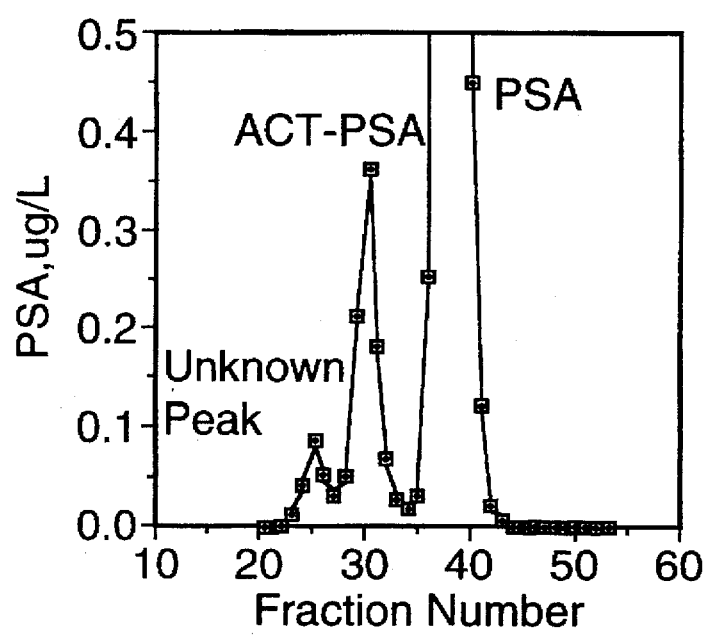

The major form of PSA (>80%) has a molecular weight identical to seminal plasma PSA, around 33 KDa. A minor form (<20%) with a molecular weight of approximately 100 KDa corresponds to PSA complexed with $\alpha_1$-antichymotrypsin (ACT) (Stenman et. al., 1991, Lilja et.

al., 1991, Christensson et. al., 1990). The identity of this peak was confirmed with an assay that specifically measures the PSA-ACT complex as previously described (Yu and Diamandis 1993, Stenman et. al., 1991, Lilja et. al., 1991, Christensson et. al., 1990). In serum, the PSA-ACT complex is the major form of PSA in accordance with previous reports (Yu and Diamandis 1993), while free PSA is a minor fraction (FIG. 4B). Another PSA-containing complex with a molecular weight of approximately 300 KDa was also seen at relatively low concentrations in some amniotic fluids but its identity was not established (FIG. 4D).

Figure 5A:
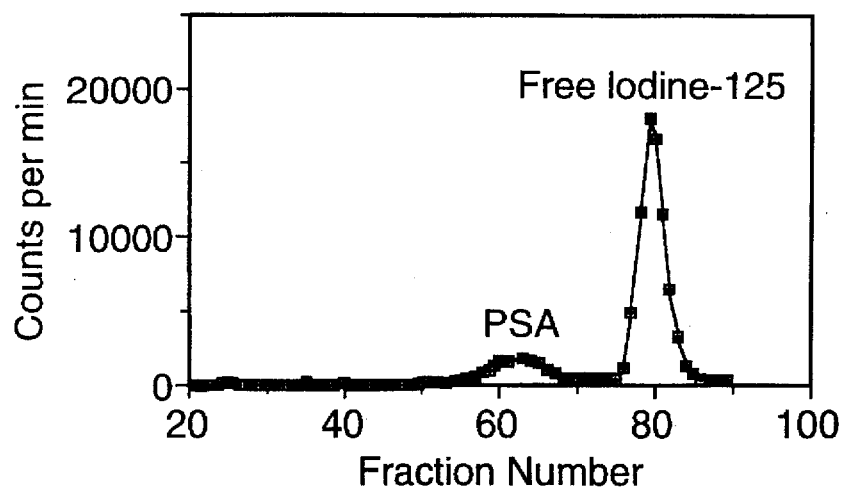
FIGS. 5A–5C: High performance liquid chromatographic 'separation of radioiodinated seminal plasma PSA diluted in Tris buffer (FIG. 5A) in amniotic fluid (FIG. 5B) or in human serum (FIG. 5C).
Figure 5B:
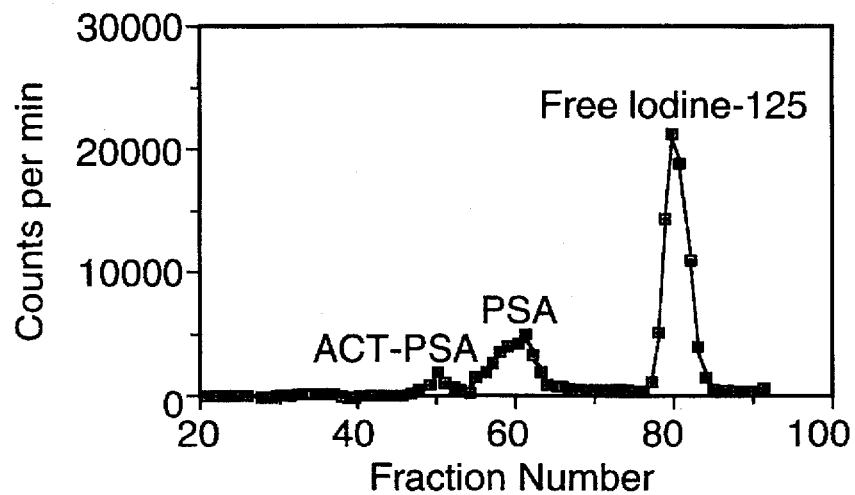
Figure 5C:
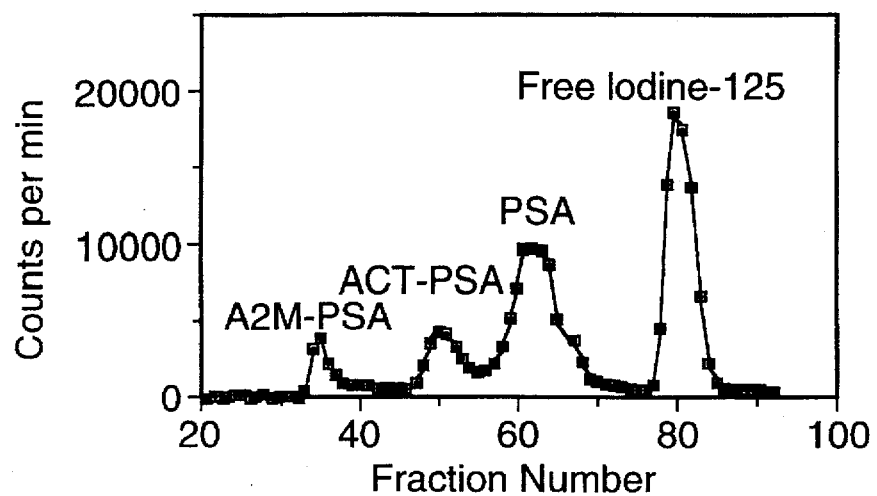

In order to examine if there are more PSA binders in amniotic fluid which could form immunologically non-measurable complexes with PSA, seminal plasma PSA was radioiodinated and its distribution examined after dilution in a Tris buffer (control), amniotic fluid or serum. Radioactive PSA added to amniotic fluid or serum was incubated for at least 1 h before injection into the HPLC gel filtration column. FIG. 5 provides the results for high performance liquid chromatographic separation of radioiodinated seminal plasma PSA diluted in Tris buffer (A) in amniotic fluid (B) or in human serum (C). Each fraction was counted for radioactivity (counts per min). Flow-rate was 0.3 mL/min. The column was calibrated with molecular weight standards eluting at fraction 34 (660 KDa), 46 (160 KDa), 57 (44 KDa), 65 (17 KDa) and 78 (1.4 KDa). Free $^{125}$I elutes at fraction 80. PSA, ACT-PSA and A2M-PSA are fractions of free PSA or PSA bound to $\alpha_1$-antichymotrypsin and $\alpha_2$-macroglobulin, respectively. Under the conditions of this experiment, free radioiodinated PSA elutes at fraction 62 corresponding to a molecular weight of 33 KDa. In amniotic fluid, a minor PSA-containing component elutes at fraction 50, with a molecular weight of 100 KDa. This corresponds to PSA bound to $\alpha_1$-antichymotrypsin. In serum, in addition to free and $\alpha_1$-antichymotrypsin-bound PSA, another PSA-containing component elutes at fraction 34 corresponding to a molecular weight of approximately 700 KDa. This complex represents PSA bound to $\alpha_2$-macroglobulin (A2M) (Stenman et. al., 1991, Lilja et. al., 1991, Christensson et. al., 1990). The A2M-PSA complex is not measurable by immunological assays for PSA. These data, and those of FIG. 4, confirm that amniotic fluid PSA is present predominantly in its free, 33 KDa form. A minor fraction exists as PSA-ACT complex. The $\alpha_2$-macroglobulin-PSA complex does not seem to exist in appreciable amounts in amniotic fluid presumably due to the absence of $\alpha_2$-macroglobulin in this fluid.

Figure 6:
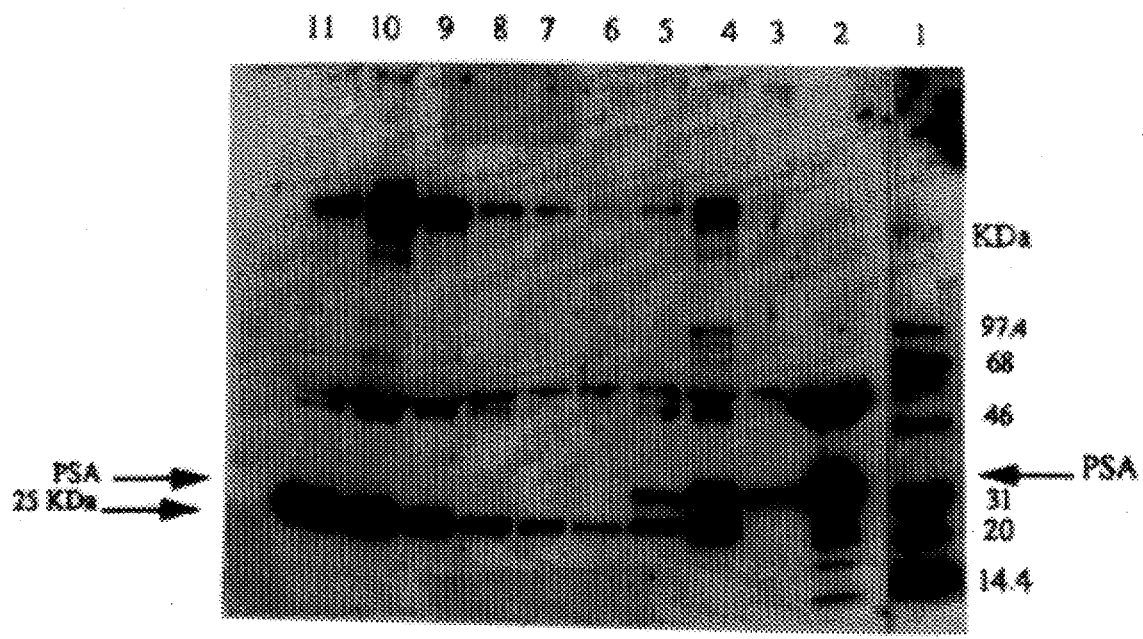
FIG. 6: Western blot analysis.

Western blot analysis of amniotic fluid, using a rabbit polyclonal anti-PSA antibody, has shown that amniotic fluid PSA appears at positions identical to those of seminal PSA or PSA produced by the prostrate cancer cell line LNCaP (FIG. 6). The brackets in FIG. 6 indicate the amount of PSA loaded per lane. Lane 1. Molecular weight markers. Lane 2. Purified seminal PSA dissolved in 10 g/L bovine serum albumin (6 ng). There is a prominent 33 KDa band (overexposed) and bands at 21, 17 and 12 KDa. Lane 3. PSA-containing supernatant from the LNCaP prostatic carcinoma cell line (0.6 ng). There is a single 33 KDa band. Lane 4. A highly PSA-positive amniotic fluid (500 µg/L) diluted 2-fold (2.5 ng). Lane 5. The amniotic fluid of lane 4 diluted 10-fold (0.5 ng). There are two prominent bands at 33 KDa (PSA) and at 25 KDa (unknown identity). Lane 6. Amniotic fluid (AF) at 11 weeks gestation (WG). Lane 7. AF at 12 WG 8. AF at 13 WG 9. AF at 15 WG 10. AF at 16 WG 11. AF at 27 WG. The amniotic fluids in lanes 6–11 had IR-PSA <2 µg/L; the loading of PSA per lane was <20 pg which is below the detection limit of the Western blot. PSA bands are visible at 33 KDa in lanes 2, 3, 4 and 5. Arrows indicate positions of PSA and of the 25 KDa band. Amniotic fluids also contain another immunoreactive band appearing at a molecular weight of approximately 25 KDa and a band at a molecular weight >200 KDa. The 25 KDa band was also found in extracts from normal breasts but not extracts from breast tumors. The identity of the 25 KDa band was not established although it was clear that it accumulates in amniotic fluid with increasing gestational age (FIG. 6).

Figure 7:
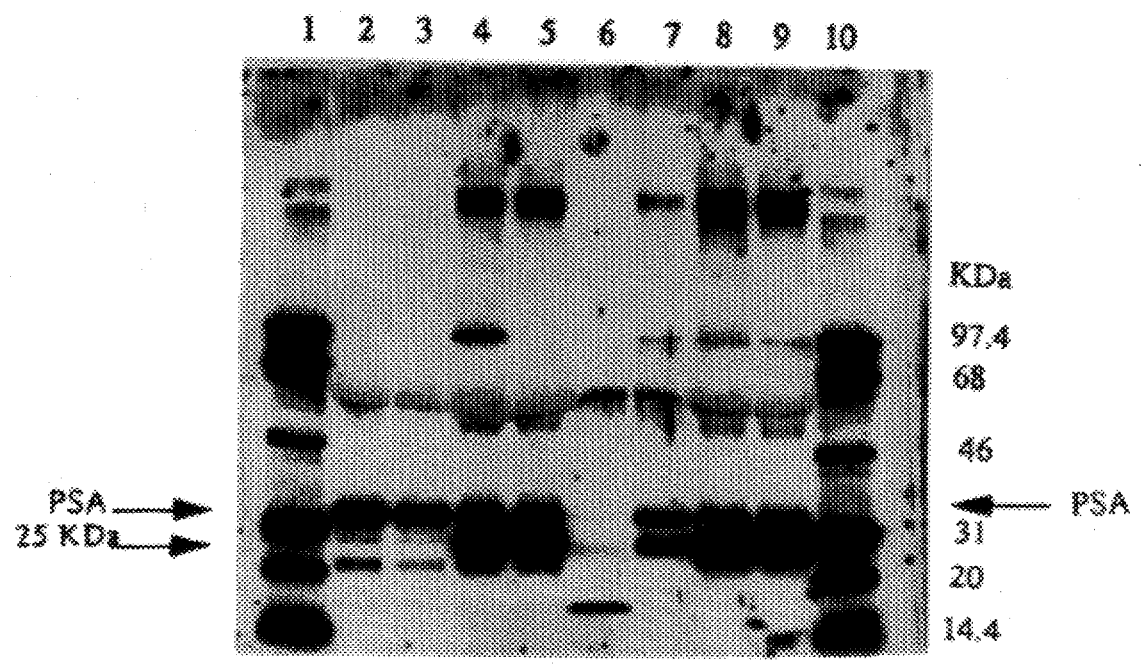
FIG. 7: Western blot analysis.
Figure 8:
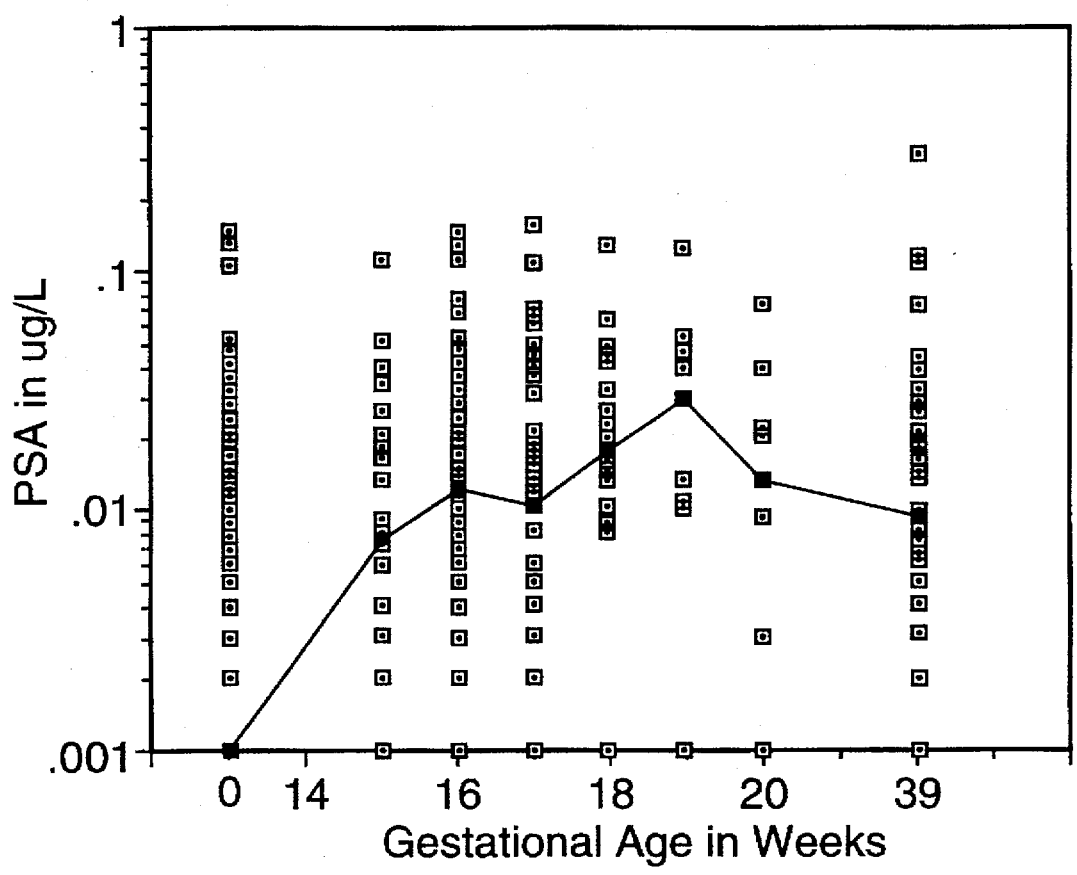
FIG. 8: PSA concentration in the serum of pregnant (N=259) and non-pregnant women (N=312) versus the completed gestational week. Non-pregnant sera are plotted at gestational week 0; sera plotted at gestational week 39 were collected at term.

The stability of PSA in amniotic fluid at 37° C. was examined. For this experiment, two amniotic fluids were spiked wih seminal PSA or PSA contained in a highly positive amniotic fluid. In one amniotic fluid, PSA was stable at 37° C. for 5 days but in the other, PSA was degraded with generation of a 16 KDa band. FIG. 7 is the Western blot analysis. In brackets is the amount of PSA loaded per lane. Lanes 1 and 10 are molecular weight markers. Lane 2. Purified seminal plasma PSA in Tris buffer, pH 7.80, stored at 30° C. for 5 days (1.2 ng). Lane 3. As in lane 2 but with storage at –70° C. Lane 4. Amniotic fluid spiked with seminal plasma PSA as in lane 2 and stored at 37° C. for 5 days. Lane 5. As in lane 4 but with storage at –70° C. Lane 6. Amniotic fluid highly positive for PSA (500 g/L) diluted 10-fold in Tris buffer, pH 7.80, and stored at 37° C. for 6 days (0.5 ng). Lane 7. As in lane 6 but with storage t –70° C. Lane 8. Amniotic fluid of lane 4 spiked with PSA contained in the amniotic fluid of lane 6 (0.5 ng) and stored at 37° C. for 5 days. Lane 9. As in lane 8 but with storage at –70° C. Notice the disappearance of PSA and the 25 KDa band in lane 6 with generation of a 16 KDa band.

The stability of PSA in amniotic fluid at –20° C. was also examined. For this experiment 12 fresh amniotic fluids were stored in aliquots at 4° C. and –20° C. for 4 months. This study revealed that PSA immunoreactivity was stable (+10%) at both temperatures. It was thus concluded that the immunoreactive PSA concentrations measured in the aliquots stored at –20° C. for about 4 months, accurately represent PSA concentrations at the time of amniocentesis.

The discovery of PSA in amniotic fluid and maternal serum enables the gestational age of the fetus to be determined. Presently gestational age is initially calculated by counting the days from the woman's last period. This may later be adjusted somewhat by monitoring fetal development and comparing this to the expected development for that age. The measurement of PSA at the time when amniocentesis is conducted will enable determination of gestational age. The measurement of PSA in amniotic fluid or maternal serum also provides an early warning system for potential problems in the fetus. PSA levels are greatly elevated in these fluids in the condition of Rhesus (Rh) incompatibility and certain fetal abnormalities. Such measurement of PSA in amniotic fluid or maternal serum provides a basis for diagnosis or screening for fetal phenotypic and/or genotypic disorders.

A high PSA level in amniotic fluid was associated with a pregnancy in which the fetus developed neonatal hyperbilirubinemia due to Rhesus incompatibility syndrome. In this case the amniotic fluid PSA level was 500 µg/L by our assay and 440 µg/L by the IMx method. This sample was drawn by amniocenesis at 30 weeks gestation. This female newborn, delivered at 38 weeks gestation was Rh(+); the mother was Rh(–) and was sensitized from a previous pregnancy. Postpartum, the newborn developed severe jaundice and needed phototherapy and exchange transfusion. No other abnormalities were present.

Further data collected also indicated that PSA under or over expression is associated with certain fetal abnormalities. Pregnancy outcomes were studied in cases where medical history reports, ultrasound reports, amniotic fluid AFP screening reports and/or surgical pathology reports were available. From the 372 cases with sufficient information, 324 pregnancies were identified and associated with normal fetuses/newborns and 48 pregnancies associated with fetuses/newborns with phenotypic/genotypic abnormalities.

It is apparent from the following discussion of the data that a comparison of the measured PSA level to the PSA mean for the particular gestational week can be made by calculating the multiple of the mean (MOM). By such comparison to the mean one is now able to classify the mother's fetus as a high or low risk for a genetic and/or phenotypic disorder. One case was a twin pregnancy (case 20) and in one pregnancy two amniotic fluid samples were taken (case 28). Table 9 sets out the fetal abnormalities identified along with gestational week, PSA concentration in amniotic fluid, the multiple median of PSA per case and the percentile of PSA concentration per gestational week for each case. Cases 1, 3, 4, 13, 15, 24, and 37 were diagnosed as trisomic. Four of them had MOM below 0.14, one had a MOM of 0.62 and two others had MOM above 1.0. The data with trisomic cases suggests that the PSA concentration in amniotic fluid, especially after gestational week 15, is significantly reduced. Another case with suspected trisomy 21 (case 42) also had a low amniotic fluid PSA. Four cases (18, 19, 33 and 46) were fetuses with anencephaly. The PSA concentration in these cases was relatively low (0.12, 0.59, 0.57 and 0.36 MOM). Two fetuses associated with renal malformations (cases 17 and 21) had very low PSA concentration in amniotic fluid (MOM of 0.006 and 0.054). From two cases of Turner's syndrome (cases 2 and 31) one had a very high amniotic fluid PSA (MOM 33.9). From other samples, notable levels of PSA were seen in cases 28 (cystic mass with large diverticulum, clubbed feet, MOM 0.036–0.002), case 10 (2 vessel cord, choroid plexus cysts, MOM 0.10), case 14 (unknown abnormality, MOM 0.20), case 29 (osteogenesis imperfecta, MOM 2.5), case 22 (hydrops, horseshoe right kidney, MOM 3.15), case 11 (Arnold-Chiari malformation, spina bifida, clubbed feet, MOM 4.7), case 30 (nuchal thickening, small stomach, palatal and labial clefts, MOM 4.84), and case 26 (unknown abnormality, MOM 13.1).

After discovering PSA in amniotic fluid and pregnant women's sera, the prostate specific antigen was tested for in breast milk during lactation, after delivery. Milk was collected between 2 and 22 days post delivery and was analyzed after centrifugation at 12,000 g for 5 min, to remove lipids. All milks tested had detectable amounts of PSA ranging from 0.01 µg/L to 330 µg/L. Among 20 milks tested, 5 had values >10 µg/L. Milk PSA was also measured by IMx PSA assay and the results between IMx and our assay for PSA were very similar. Western blot analysis confirmed the presence of PSA and HPLC analysis demonstrated that most PSA was present in the 33 KDa form; a small proportion (<10%) was present as PSA-$\alpha_1$-antichymotrypsin complex. The highest PSA concentration was present in milks collected two days after delivery. After the 6th day, PSA levels in milk decline to very low levels.

The measurement of PSA in breast milk is useful for assessing the amount of steroids circulating in the blood of a woman post-delivery and the rate of their metabolism, if PSA is monitored in the milk with serial measurements.

MATERIALS AND METHODS

Samples

Amniotic fluids used were leftovers from routine amniotic fluid alpha-fetoprotein or bilirubin analysis for diagnosis of neural tube defects or haemolytic syndromes, respectively, and were provided by Dr. L. Allen, Department of Clinical Biochemistry, The Toronto Hospital. Amniotic fluids at term, collected during labour, were provided by Dr. V. Davies, Toronto East General Hospital. The amniotic fluids were kept frozen at −20° C. until analysis. Cord blood was collected just after delivery in tubes without any anticoagulant. Cord blood serum and maternal serum was separated and stored at −20° C. until analysis (<3 weeks).

Methods

PSA determinations were carried out with an ultrasensitive assay described in detail in (Yu and Diamandis 1993) and reproduced below. For comparative studies we have also used a commercially available automated PSA assay (IMx, Abbott Laboratories, Chicago, Ill.) (Vessela et. al., 1992). High performance liquid chromatography and Western blot analysis for PSA were performed essentially as described elsewhere (Yu et. al., 1994, Yu and Diamandis 1993). Highly purified seminal plasma PSA, a gift from Dr. T. Stanmey, Stanford University, was radioiodinated with $^{125}$I using iodobeads, commercially available from Pierce Chemical Co., Rockford, Ill. The procedure recommended by the manufacturer was followed, and the bulk of non-incorporated $^{125}$I was removed by gel filtration on disposable PD-10 Sephadex columns (Pharmacia, Uppsala, Sweden). The LNCaP cell line cultured as previously described (Yu et. al., 1994)

ULTRASENSITIVE PSA ASSAY

Instrumentation

For measuring liquid-phase $Tb^{3+}$ fluorescence in white microtiter wells, we used the Cyberfluor (Toronto, Canada) 615® Immunoanalyzer, a time-resolved fluorometer. The time-gate settings of the instrument and the interference filter in the emission pathway have been described elsewhere (Milgrom 1992, Foekens et. al., 1990).

Reagents and solutions

All reagents were purchased from Sigma Chemical Co., St. Louis, Mo., unless otherwise stated. The coating solution was 50 mmol/L Tris buffer, pH 7.80, containing 0.5 g of sodium azide per liter. The wash solution was 5 mmol/L Tris buffer, pH 7.80, containing 0.15 mol of NaCl and 0.5 g of polyoxyethylenesorbitan monolaurate (Tween 20) per liter. The substrate buffer was 0.1 mol/L Tris buffer, pH 9.1, containing 0.15 mol of NaCl, 1 mmol of $MgCl_2$, and 0.5 g of sodium azide per liter. The substrate stock solution was a 10 mmol/L diflunisal phosphate (DFP) solution in 0.1 mol/L NaOH, available from Cyberfluor. The developing solution contained 1 mol of Tris base, 0.4 mol of NaOH, 2 mmol of $TbCl_3$, and 3 mmol of EDTA per liter (no pH adjustment). This solution was prepared as described previously (Weber et. al., 1989, Wei 1993) and is commercially available from Cyberfluor. The assay buffer was 50 mmol/L Tris buffer, pH 7.80, containing 60 g of BSA, 0.5 mol of KCl, 0.5 g of sodium azide, 50 mL of normal mouse serum, 5 mL Tween 20 and 5 g of Triton X-100 per liter. The diluent for the polyclonal biotinylated detection antibody and alkaline phosphatase-conjugated streptavidin (SA-ALP) was 50 mmol/L Tris buffer, pH 7.80, containing 60 g of BSA per liter. The diluent for alkaline phosphatase-conjugated goat anti-rabbit IgG (GARIg-ALP) was the same as for the polyclonal biotinylated detection antibody but also contained 40 mL/L goat serum. The blocking solution was 50 mmol/L Tris buffer, pH 7.80, containing 10 g of BSA per liter.

Antibodies

The mouse monoclonal (MBPO405) and the rabbit polyclonal (PBP0101) anti-PSA antibodies were purchased from Medix Biotech, Foster City, Calif. The SA-ALP conjugate was purchased from Jackson ImmunoResearch, West Grove, Pa., as was the affinity purified, Fc fragment-specific GARIg-ALP. A polyclonal rabbit antibody against ACT was purchased from Dakopatts (Glostrup, Denmark).

Standards

Because of the unavailability of a universally accepted standard for PSA, we used PSA standards in 50 mmol/L Tris buffer, pH 7.80, containing 60 g/L BSA. A stock PSA solution containing PSA purified from human seminal plasma was purchased from Scripps Laboratories, San Diego, Calif. Our final standard solutions were calibrated against standards from the Hybritech Tandem-PSA kit. For routine use we recommend six PSA standards, at concentrations 0, 0.025, 0.1, 0.5, 2, and 10 µg/L. These are stable for at least 1 month at 4° C.

Comparison method and patients' samples

For comparison we used the Tandem-PSA enzyme immunoassay kit from Hybritech. Patients' samples analyzed by the Hybritech assay were stored at −70° C. for < month.

Biotinylation of polyclonal anti-PSA antibody

The polyclonal anti-PSA antibody, purified by ion-exchange chromatography, was dialyzed overnight against 5 L of a 0.1 mol/L sodium bicarbonate solution. This stock antibody solution (~2 g/L) was diluted twofold with 0.5 mol/L carbonate buffer, pH 9.1. To this solution we added 1 mg of the N-hydroxysuccinimide ester of biotin (NHS-LC-Biotin; Pierce Chemical Co., Rockford, Ill.) dissolved in 50 µL of dimethyl sulfoxide and incubated it for 2 h at room temperature with continuous stirring. This biotinylated antibody was used without further purification and could be stored without loss at 4° C. for at least 6 months.

Coating of microliter wells

White, opaque 12-well microtiter polystyrene strips were obtained from Dynatech Laboratories, Alexandria, Va. The wells were coated overnight at room temperature with monoclonal anti-PSA antibody in the coating buffer, 5 mg/L. Before use, the wells were washed twice and blocked for 1 h with 200 µL per well of the blocking solution.

Assay procedure

Wash the strips six times. Into each well pipet 50 uL of amniotic fluid sample, breast milk sample, serum sample or PSA standards and add 50 µL of assay buffer per well. Incubate for 3 h at room temperature with continuous mechanical shaking; then wash six times. Add 100 µL per well of the biotinylated rabbit polyclonal detection antibody, diluted 100-fold in the polyclonal detection antibody diluent (100 ng of antibody per well). Incubate for 1 h as above and then wash six times. All 100 µL per well of SA-ALP conjugate, diluted 30,000-fold in the SA-ALP diluent (3 ng of conjugate per well). Incubate for 15 min as above and then wash six times. Add 100 µL per well of the DFP substrate, diluted 10-fold just before use in the substrate buffer (working DFP substrate solution, 1 mmol/L) and incubate for 10 min at room temperature with shaking. Add 100 µL per well of the developing solution, mix by shaking for 1 min, and read the $T^{3+}$-specific fluorescence with the Cyberfluor 615 Immunoanalyzer. Data reduction is performed automatically.

Assay for the PSA-ACT complex

This assay is the same as the PSA assay described above but, instead of using the biotinylated polyclonal rabbit anti-PSA antibody, we used the polyclonal rabbit ACT antibody, diluted 500-fold in the SA-ALP conjugate diluent. We then added 100 µL of 5000-fold-diluted GARIG-ALP conjugate (20 ng per well) and incubated for 30 min with shaking. After washing the wells six times, we completed the assay by adding the DFP substrate as described in the PSA assay. No effort was made to calibrate this assay because of the unavailability of standard PSA-ACT complex.

HPLC

HPLC was performed with a Shimadzu system with an absorbance monitor at 280 nm (Shimadzu Corp., Kyoto, Japan). The mobile phase was a 0.1 mol/L $Na_2SO_4$-0.1 mol/L $NaH_2PO_4$ solution, pH 6.80. The flow rate was 0.3 mL/min and the HPLC was run isocratically. The gel-filtration column was a Bio-Sil SEC-250 column, 600×7.5 mm (Bio-Rad Labs., Richmond, Calif.). The column was calibrated with a molecular mass standard solution from Bio-Rad, containing thyroglobulin (670 kDa), IgG (158 kDa), ovalbumin (44 kDa), myoglobulin (17 kDa), and cyanocobalamin (1.4 kDa). HPLC fractions (0–3 mL) were collected with a fraction collector (Model FRAC-100; Pharmacia, Uppsale, Sweden).

REFERENCES

1. Osterling J. E. Prostate specific antigen: a critical assessment of the most useful tumor marker for adenocarcinoma of the prostate. J. Urol 1991; 145: 907–23.
2. Armbruster D. A. Prostate-specific antigen: biochemistry, analytical methods, and clinical application. Clin Chem 1993; 39: 181–95.
3. Cohen P., Graves H. C. B., Peehl D. M., Kamarei M., Giudice L. C., Rosenfeld R. G. Prostate-spec@@fic antigen (PSA) is an insulin-like growth factor binding protein-3 protease found in seminal plasmel. J Clin Endocrinol Metab 1992; 75: 1046–53.
4. Kanety H., Madjar Y., Dagari Y., Levi J., Papa M. Z., Pariente C., Goldwasser B., Karasik A. Serum insulin-like growth factor-binding protein-2 (IGFBP-2) is increased and IGFBP-3 is decreased in patients with prostate cancer: correlation with serum prostate-specific antigen. J Clin Endocrinol Metab 1–993; 77: 229–33.
5. Killian C. S., Corral D. A., Kawinski E., Constantine R. I. Mitogenic response of osteoblast cells to prostate-specific antigen suggests an activation of latent TGF-B and a proteolytic itiodulation of cell adhesion receptors. Biochem Biophys Res Commun 1993; 192: 940–47.
6. Espana F., Gilabert J., Estelles A., Romeu A., Asnar J., Cabo A. Functionally active protein C inhibitor/plasminogen activator inhibitor-3 (PCI/PAI-3) is secreted in seminal vesicles, occurs at high concentrations in human seminal plasma and complexes with prostate-specific antigen. Thrombosis Res 1991; 64: 309–20.
7. Ashwood E. R. Clinical chemistry of pregnancy. In: Burtis C. A., Ashwood E. R., editors. Tietz Textbook of Clinical Chemistry, Second Edition. Philadelphia. W.P. Saunders 1994: 2107–48.
8. Diamandis, E. P. Immunoassays with time-resolved fluorescence spectroscopy. Principles and applications. Clin. Biochem., 1988; v. 21: pp. 139–150.
9. He, Y., Diamandis, E. P. Ultrasensitive time-resolved immunofluorometric assay of prostratespecific antigen in serum Clin. Chem., 1993 (in press).

10. Yu H. and Diamandis E. P. Ultrasensitive Time-resolved immuno-fluorometric assay of prostate specific antigen in serum and preliminary clinical studies. Clin Chem 1993; 39: 2108–14.

11. Vessela R. L., Noteboom J., Lange P. H. Evaluation of the Ahbott IMXR automated immunoassay of prostate-specific antigen. Clin Chem 1992; 38: 2044–54.

12. Yu H., Diamandis E. P. and Grass L., Induction of prostate specific antigen production by steroids and tamoxifen in breast cancer cell-lines. Breast Cancer Res Treat (in press) (1994).

13. Diamandis E. P., Yu H. and Sutherland D. J. A. Detection of prostate specific antigen immunoreactivity in breast tumors. Breast Cancer Res Treat (in press) (1994).

14. Yu H., Diamandis E. P. and Sutherland D. J. A. Immunoreactive prostate specific antigen levels in female and male breast tumors and its association with steroid hormone receptors and patient age. Clin Biochem 1994; 27: 75–79.

15. Yu H. and Diamandis E. P. Serum prostate specific antigen levels after radical prostatectomy and in women. Submitted (1994).

16. Kamoshida S., Tsutsumi Y. Extraprostatic localization of prostate acid phosphatase and prostate-specific antigen: distribution in cl-oacogenic glandular epithelium and sex-dependent expression in human anal gland. Hum Pathol 1990; 21: 1108–11.

17. Frazier H. A., Humphrey P. A., BurchetLe J. I., Paulson D. F. Immunoreactive prostatic specific antigen in male periurethral glands. J Urol 1992; 147: 246–48.

18. Iwakiri J., Grandbois K., Wehrier N., Graves H. C. B., Stamey T. An analysis of urinary prostatic specific antigen before and after radical prostatectomy: evidence for secretion of prostate specific antigen by the periurethral glands. J Urol 1993; 149: 783–86.

19. Stenman U-H., Leinonen J., Alfthan H., Rannikko S., Tuhkanen K., Alfthan O. A complex between prostate-specific antigen and $a_1$-antichymotrypsin is the major form of prostate-specific antigen in serum of patients with prostatic cancer: assay of the complex improves clinical sensitivity for cancer. Cancer Res 1991; 51: 222–6.

20. Lilja H., Christensson A., Dahlen. I. J., Matikainen M. T., Nilsson O., Pettersson K., Lovgren T. Prostate-specific antigen in serum occurs predominantly in complex with $a_1$-antichymotrypsin. Clin Chem 1991; 37: 1618–25.

21. Christensson A., Laurell C. B., Lilja H. Enzymatic activity of the prostate-specific antigen and its reactions with extracellular serine protease inhibitors. Eur J Biochem 1990; 194: 755–63.

22. Milgrom, E. The oestrogen-regulated $pS_2$-BCEI protein in breast cancer. In: Coldhirsch, A., ed. Endocrine therapy of breast cancer V. Berlin: Springer Verlag, 1992: 17–22.

23. Foekens, J. A., Rio, M. C., Segiiin, P., et al. Prediction of relapse and survival in breast cancer patients by $pS_2$, protein status. Cancer Res., 1990; 50: 3832–7.

24. Weber, J. P., Oesterling, J. E., Peters, C. A., Partin, A. W., Chan, D. W., Walsh, P. C. The influence of reversible androgen deprivation on serum prostate-specific antigen levels in men with benign prostate hyperplasia. J. Urol., 1989; 141: 987–91.

25. Wei, L. L. Transcriptional activation of the estrogen receptor. Clin. Chem., 1993; 39: 341–45.

TABLE 1

Recovery of PSA Added to Amniotic Fluids.

| PSA, μg/L Initially Present | Added | Recovered[c] | % Recovery |
|---|---|---|---|
| 3.30 | 6.48[a] | 4.62 | 71 |
| 1.82 | 6.48 | 5.45 | 84 |
|  | 10.28 | 7.71 | 75 |
| 0.76 | 6.48 | 6.43 | 100 |
|  | 10.28 | 8.53 | 83 |
| 0.64 | 6.48 | 6.46 | 100 |
|  | 10.28 | 8.74 | 85 |
| 1.66 | 7.95[b] | 7.65 | 96 |
| 0.87 | 7.95[b] | 7.79 | 98 |
| 0.68 | 7.95[b] | 8.59 | 108 |

[a]Addition of seminal plasma PSA except as indicated otherwise.
[b]Addition of PSA present in the serum of a prostate cancer patient
[c]The recovered amount was calculated by subtracting the initially present concentration from the measured concentration after the spike.

TABLE 2

Dilution Linearity of the PSA Assay for Amniotic Fluids and Serum

| Sample | | Dilution Factor[a] | | | | | |
|---|---|---|---|---|---|---|---|
|  |  | None | 2 | 4 | 8 | 16 | 32 |
| Serum |  | 3.11 | 1.53 | 0.73 | 0.36 | 0.18 | 0.098 |
| Amniotic Fluid | A | ND[b] | 3.66 | 2.09 | 1.13 | 0.58 | 0.31 |
|  | B | >10 | 8.29 | 5.40 | 3.00 | 1.45 | 0.74 |
|  | C | 6.07 | 3.70 | 2.60 | 1.40 | 0.78 | 0.42 |
|  | D | 2.44 | 1.38 | 0.80 | 0.40 | 0.21 | 0.12 |

[a]All PSA values are in μg/L
[b]Not done due to sample depletion.

TABLE 3

Linear Correlation Studies for 107 Amniotic Fluids

| Y | X | Linear Regression | Correlation Coefficient | P Value |
|---|---|---|---|---|
| AF IR-PSA[1] | AF AFP[2] | y = 2.46 − 0.091x | 0.28 | 0.003 |
|  | Gestational Age[3] | y = −4.92 + 0.39x | 0.41 | <0.001 |
|  | Maternal Age[4] | y = 2.45 − 0.042x | 0.08 | 0.43 |
| AF AFP | Gestational Age | y = 42.2 − 1.68x | 0.58 | <0.001 |
|  | Maternal Age | y = −3.1 + 0.55x | 0.33 | 0.001 |

[1]AF IR-PSA = amniotic fluid immunoreactive PSA in μg/L
[2]AF AFP = amniotic fluid AFP in mg/L
[3]Gestational age in weeks
[4]Maternal age in years

TABLE 4

AFP and PSA Levels in Amniotic Fluids and Maternal Sera with Elevated AFP

|  | Gestational Age (weeks) | AFP, mg/L | MOM, AFP | PSA, μg/L | MOM, PSA |
|---|---|---|---|---|---|
| Amniotic Fluid A | 17 | 35.3 | 3.2 | 8.69 | 11.6 |
| Amniotic Fluid B | 17 | 119 | 10.7 | 0.19 | 0.25 |
| Amniotic Fluid C | 21 | 84.5 | 16.6 | 0.56 | 0.23 |
| Amniotic Fluid D | 16 | 282 | 21.4 | 0.60 | 1.9 |

TABLE 4-continued

AFP and PSA Levels in Amniotic Fluids and Maternal Sera with Elevated AFP

|  | Gestational Age (weeks) | AFP, μg/L | MOM, AFP | PSA, μg/L |
|---|---|---|---|---|
| Maternal Serum A | 19 | 496 | 9.6 | 0.007 |
| Maternal Serum B | 15 | 167 | 4.8 | 0.007 |
| Maternal Serum C | 17 | 221 | 5.4 | 0.067 |
| Maternal Serum D | 16 | 159 | 4.2 | 0.002 |

MOM = multiples of median for this gestational age.

TABLE 5

PSA Levels in Amniotic Fluid at Term

| Patient | PSA, μg/L | Abstinence from Sex, Weeks (1) |
|---|---|---|
| A | 0.51 | 20 |
| B | 0.099 | 4 |
| C | 0.13 | 4 |
| D | 0.086 | 1 |
| E | 0.059 | 1 |
| F | 1.04 | 4 |

(1) Weeks before delivery; all were physiological deliveries at 40 ± 2 weeks gestation.

TABLE 6

Prostate Specific Antigen (PSA) and Alpha-Fetoprotein (AFP) Concentrations in Amniotic Fluid per Gestational Week

| Gestational Week[1] | Sample Number | Median PSA, μg/L (95% Confidence Interval)[2] | Median AFP, mg/L (95% Confidence Interval)[2] |
|---|---|---|---|
| 11 | 25 | 0.001(0.001–0.0048) | 16.4(14.9–17.9) |
| 12 | 36 | 0.022(0.008–0.028) | 19.4(18.0–20.0) |
| 13 | 14 | 0.048(0.015–0.20) | 19.8(16.2–22.9) |
| 14 | 101 | 0.19(0.16–0.26) | 19.1(18.1–19.9) |
| 15 | 216 | 0.22(0.18–0.27) | 16.8(16.2–17.4) |
| 16 | 141[3] | 0.24(0.19–0.29) | 14.9(14.1–15.7) |
| 17 | 89 | 0.28(0.22–0.49) | 11.6(10.7–12.9) |
| 18 | 59 | 0.33(0.19–0.56) | 10.4(9.3–11.8) |
| 19 | 38 | 0.66(0.50–1.27) | 7.6(6.3–8.3) |
| 20 | 26[4] | 0.55(0.26–1.36) | 7.9(6.5–9.8) |
| 21 | 12 | 0.57(0.20–1.89) | 4.9(4.0–7.3) |
| 22 | 9 | 0.98(0.28–2.33) | 4.5(2.7–9.0) |
| 23 | 6 | 0.31(0.14–2.66) | ND[8] |
| 24 | 2[5] | 0.67[7] | 4.4 |
| 25 | 3[6] | 2.13 | 5.2 |
| 26 | 3 | 0.81 | ND |
| 27 | 4 | 0.79 | ND |
| 28 | 1 | 1.42 | ND |
| 29 | 8 | 0.88(0.25–3.04) | ND |
| 30 | 1 | 0.38 | ND |
| 31 | 3 | 0.88 | ND |
| 32 | 2 | 1.82 | ND |
| 33 | 2 | 1.95 | ND |
| 34 | 6[5] | 0.70(0.12–1.94) | 1.0 |
| 35 | 6 | 1.05(0.13–3.17) | ND |
| 37 | 1 | 1.81 | ND |
| 39 | 16 | 0.37(0.24–0.72) | ND |

[1] based on completed gestational weeks.
[2] based on the gestational week median, and calculated with the sign test, a non-parametric procedure, using Minitab 8 software.
[3] 140 samples for AFP data.
[4] 25 samples for AFP data.
[5] one sample for AFP data.
[6] 2 samples for AFP data.
[7] 95% confidence interval has not been calculated when sample number was less than six.
[8] ND, no data available for these gestational ages.

TABLE 7

Prostate Specific Antigen Concentration in the Serum of Non-Pregnant and Pregnant Women

| Gestational Week[1] | Sample Number | Median, μg/L (95% Confidence Interval)[2] | p-value[3] | Ratio (AF-PSA/MS-PSA)[4] |
|---|---|---|---|---|
| Non-pregnant | 312[5] | 0.001(0.001–0.002) | — | — |
| 15 | 36 | 0.0075(0.0027–0.013) | 0.0002 | 29.9 |
| 16 | 91 | 0.012(0.0087–0.017) | <0.0001 | 19.9 |
| 17 | 45 | 0.010(0.0055–0.014) | <0.0001 | 28.1 |
| 18 | 21 | 0.017(0.0097–0.034) | <0.0001 | 19.4 |
| 19 | 10 | 0.028(0.011–0.048) | <0.0001 | 23.0 |
| 20 | 9 | 0.013(0.0015–0.034) | 0.0079 | 42.0 |
| 39 | 47 | 0.009(0.007–0.019) | <0.0001 | 41.1 |

[1] based on completed gestational weeks.
[2] based on the gestational week median, and calculated with the sign test; a non-parametric procedure.
[3] Mann-Whitney test comparing median serum PSA concentration between non-pregnant women and women at various gestational weeks.
[4] AF-PSA, amniotic fluid PSA concentration; MS-PSA, maternal serum PSA concentration.
[5] 167 samples (54%) had the value of 0.001 μg/L or lower.

TABLE 8

Association Between Amniotic Fluid Prostate Specific Antigen Concentration and Fetal Gender

| Fetal Gender | Amniotic Fluid PSA, µg/L[1] | | | | Median PSA, µg/L (95% C.I.)[2] |
|---|---|---|---|---|---|
| | <0.098 | 0.098–0.22 | 0.23–0.55 | >0.55 | |
| Female(N = 73) | 15(20.6%) | 16(21.9%) | 18(24.7%) | 24(32.9%) | 0.37(0.19–0.51) |
| Male(N = 84) | 20(23.8%) | 20(23.8%) | 22(26.2%) | 22(26.2%) | 0.24(0.19–0.35) |

[1]$X^2 = 0.88$, degrees of freedom = 3, p = 0.83 for the Chi-square test comparing PSA distribution in male and female fetuses.
[2]p = 0.43, median comparison by the Mann-Whitney test; C.I. = confidence interval.

TABLE 9

Fetal Abnormalities and Amniotic Fluid Prostate Specific Antigen (PSA)

| Case # | Fetal Abnormality | Gest. week | PSA in µg/L | PSA MOM[1] | Ranking Percentage[2] |
|---|---|---|---|---|---|
| 1 | Down's Syndrome | 12 | 0.003 | 0.136 | 19.4 |
| 2 | Turner's Syndrome | 12 | 0.747 | 33.95 | 100 |
| 3 | Down's Syndrome | 13 | 0.151 | 3.179 | 71.4 |
| 4 | Down's Syndrome | 14 | 0.217 | 1.118 | 53.5 |
| 5 | Demise of fetus; no positive fetal heart | 14 | 0.324 | 1.67 | 72.3 |
| 6 | Moderate nuchal swelling, oligohydramnios, clubbed feet | 15 | 0.11 | 0.491 | 25.9 |
| 7 | Omphalocelel containing liver, gut and part of stomach | 15 | 0.06 | 0.268 | 11.6 |
| 8 | Large fetal cerebellum | 16 | 0.183 | 0.766 | 39.7 |
| 9 | Arnold-Chiari malformation | 16 | 0.119 | 0.498 | 23.4 |
| 10 | 2 vessel cord, large bilateral choroid plexus cysts | 16 | 0.025 | 0.105 | 5.0 |
| 11 | Arnold-Chiari malformation, spina bifida, clubbed feed | 16 | 1.126 | 4.71 | 94.3 |
| 12 | Hydrocephalus | 16 | 0.232 | 0.97 | 48.2 |
| 13 | Down's Syndrome | 16 | 0.006 | 0.025 | 1.4 |
| 14 | AF-AFP screening states that it has abnormal ultrasound (3) | 16 | 0.047 | 0.197 | 7.8 |
| 15 | Trisomy 18 | 17 | 0.019 | 0.068 | 2.25 |
| 16 | Dandy-Walker Syndrome | 17 | 0.49 | 1.74 | 61.8 |
| 17 | Nuchal hygroma, anasarca, hydronephrosis | 18 | 0.002 | 0.006 | 1.69 |
| 18 | Anencephaly | 18 | 0.038 | 0.115 | 5.08 |
| 19 | Anencephaly | 18 | 0.196 | 0.594 | 40.7 |
| 20 | Chromosomal abnormality in one of the twins | 18 | 0.453 | 1.37 | 59.3 |
| 20 | Neural tube defect with spina bifida, hydrocephaly | 18 | 0.617 | 1.869 | 67.8 |
| 21 | Multicystic renal dysplasia, low set ears, infraobital folds | 18 | 0.018 | 0.054 | 3.39 |
| 22 | Hydrops, horseshoe right kidney, 11 ribs on one side | 18 | 1.041 | 3.15 | 77.97 |
| 23 | Large bilateral choroid plexus cysts (1 and 2 cm) | 18 | 0.262 | 0.794 | 49.2 |
| 24 | Down's Syndrome, Rh positive | 18 | 0.205 | 0.621 | 42.4 |
| 25 | Large echogenic kidneys, 11 pairs of ribs | 18 | 0.476 | 1.442 | 61 |
| 26 | AF-AFP screening states that is has abnormal ultrasound (3) | 18 | 4.334 | 13.13 | 94.9 |
| 27 | Arnold-Chiari type of signs, with neural tube defects | 18 | 0.097 | 0.294 | 23.7 |
| 28 | Cystic mass with large diverticulum, clubbed feet | 19 | 0.024 | 0.036 | 2.63 |
| 28 | Cystic mass with large diverticulum, clubbed feet | 21 | 0.001 | 0.002 | 8.3 |
| 29 | Osteogenesis imperfecta | 19 | 1.642 | 2.5 | 84.2 |
| 30 | Nuchal thickening, small stomach, palatal & labial clefts | 19 | 3.175 | 4.84 | 92.1 |
| 31 | Turner's Symdrome | 19 | 0.23 | 0.351 | 18.4 |
| 32 | Osteogenesis imperfecta | 19 | 0.609 | 0.928 | 44.7 |
| 33 | Anencephaly | 19 | 0.373 | 0.568 | 26.3 |
| 34 | Borderline thickening of nuchal fold | 20 | 0.553 | 1.013 | 53.8 |
| 35 | Cystic hygroma in the posterior nuchal region | 20 | 0.405 | 0.742 | 42.3 |
| 36 | Midline defect in cerebellum, suspicion of Dandy-Walker S. | 20 | 0.121 | 0.222 | 15.4 |
| 37 | Down's Syndrome | 21 | 0.066 | 0.115 | 16.7 |
| 38 | AF-AFP report indicated ultrasound abnormality, stillbirth (3) | 21 | 0.19 | 0.332 | 25.0 |
| 39 | Amniotic band Syndrome; exencephaly | 21 | 0.24 | 0.419 | 41.7 |
| 40 | Arnold-Chiari malformation, spina bifida | 21 | 0.67 | 1.17 | 58.3 |
| 41 | Semilobular holoprosencephalus, neural tube defect, cord abn. | 22 | 0.657 | 0.668 | 44.4 |
| 42 | Borderline of nuchal fold increase, suspision of Trisomy 21 | 22 | 0.087 | 0.088 | 11.1 |
| 43 | Hydrocephalus, polyhydromnios, atrial septal defect | 22 | 0.626 | 0.636 | 33.3 |
| 44 | Arnold-Chiari malformation; lemon shaped head | 22 | 0.984 | 1.00 | 55.6 |
| 45 | Chiari malformation, ventriculomegaly, clubbed feet | 23 | 0.196 | 0.626 | 50.0 |
| 46 | Anencephaly | 23 | 0.112 | 0.358 | 16.7 |
| 47 | Lemon shaped head, open neural tube defect, clubbed feet | 23 | 0.193 | 0.617 | 33.3 |
| 48 | Microcephaly; no cerebral hemispheres, hydranencephaly | 25 | 0.624 | 0.425(4) | 33.3 |

[1]MOM = multiples of median for the corresponding gestational week.
[2]Ranking % = rank # of AF-PSA concentration (increasing order, adjusted for ties)/sample # x100; ratio for corresponding gestational week.
(3)Cases listed with unspecified fetal abnormalities whose AF-AFP MOM (ascending case #) are; 1.17, 0.44, and 1.39.
(4)Calculated with corresponding AF-PSA median of 1.468 (median estimated by presumptive interpolation of the figure 1 median curve)

The embodiments of the invention in which an exclusive property or privilege is claimed are defined as follows:

1. A prenatal evaluation of fetal phenotypic and/or genotypic disorders, comprising the steps of:
   i) providing a sample of amniotic fluid or maternal serum from a pregnant woman in a gestational week;
   ii) conducting a biological assay of said sample to detect the presence of prostate specific antigen;
   iii) upon quantifying the level of prostate specific antigen in said sample, comparing said prostate specific antigen with the prostate specific antigen mean for the gestational week; and
   iv) classifying said pregnant woman as a high or low-risk for carrying a fetus with a phenotypic and/or genotypic disorder.

2. The prenatal evaluation of claim 1, said sample being amniotic fluid.

3. The prenatal evaluation of claim 2, wherein said biological assay comprises time resolved fluorometry and detecting concentrations of at least 0.01 µg/L of prostate specific antigen in said sample.

4. The prenatal evaluation of claim 2, wherein said biological assay comprises binding of a monoclonal or polyclonal antibody specific for prostate specific antigen or prostate specific antigen complex to prostate specific antigen or prostate specific antigen complex in said sample.

* * * * *